United States Patent
Mimura

(10) Patent No.: US 10,890,576 B2
(45) Date of Patent: Jan. 12, 2021

(54) IMAGE PROCESSING DEVICE, IMAGE PROCESSING METHOD, AND RECORDING MEDIUM

(71) Applicant: Konica Minolta, Inc., Tokyo (JP)

(72) Inventor: Yusuke Mimura, Hino (JP)

(73) Assignee: Konica Minolta, Inc., Tokyo (JP)

( * ) Notice: Subject to any disclaimer, the term of this patent is extended or adjusted under 35 U.S.C. 154(b) by 106 days.

(21) Appl. No.: 16/311,781

(22) PCT Filed: May 17, 2017

(86) PCT No.: PCT/JP2017/018453
§ 371 (c)(1),
(2) Date: Dec. 20, 2018

(87) PCT Pub. No.: WO2017/221592
PCT Pub. Date: Dec. 28, 2017

(65) Prior Publication Data
US 2019/0204292 A1    Jul. 4, 2019

(30) Foreign Application Priority Data

Jun. 23, 2016  (JP) ................. 2016-124037

(51) Int. Cl.
*G06K 9/00* (2006.01)
*G01N 33/483* (2006.01)
(Continued)

(52) U.S. Cl.
CPC ........ *G01N 33/4833* (2013.01); *G01B 11/24* (2013.01); *G01N 33/48* (2013.01);
(Continued)

(58) Field of Classification Search
None
See application file for complete search history.

(56) References Cited

U.S. PATENT DOCUMENTS 4,097,845 A * 6/1978 Bacus ............... G06K 9/00127
                                                    348/79
5,548,661 A * 8/1996 Price .................. G01N 15/147
                                                    348/80
(Continued)

FOREIGN PATENT DOCUMENTS

EP     2779089 A2    9/2014
JP   H07-198714 A    8/1995
(Continued)

OTHER PUBLICATIONS

International Preliminary Report on Patentability issued in parent PCT Application No. PCT/JP2017/018453, dated Dec. 25, 2018.
(Continued)

*Primary Examiner* — Shervin K Nakhjavan
(74) *Attorney, Agent, or Firm* — BakerHostetler

(57) ABSTRACT

There is provided an image processing device including an input receiver of inputting an image obtained by photographing a specimen subjected to staining and a hardware processor. The hardware processor extracts a region subjected to the staining from the image as a cell region; extracts a region as a candidate region, the region being surrounded by the cell region and not being subjected to the staining. The hardware processor further extracts a feature amount of the candidate region; determines whether or not the candidate region is a cell region on a basis of the feature amount; and corrects the candidate region which is determined to be a cell region by the distinction means to be a cell region.

9 Claims, 10 Drawing Sheets

(51) Int. Cl.
*G01B 11/24* (2006.01)
*G06T 7/60* (2017.01)
*G01N 33/48* (2006.01)
*G06T 7/00* (2017.01)
*G06T 7/62* (2017.01)
*G06T 5/50* (2006.01)

(52) U.S. Cl.
CPC .............. *G01N 33/483* (2013.01); *G06T 5/50* (2013.01); *G06T 7/00* (2013.01); *G06T 7/60* (2013.01); *G06T 7/62* (2017.01)

(56) References Cited

U.S. PATENT DOCUMENTS

| | | | | |
|---|---|---|---|---|
| 7,760,927 | B2 * | 7/2010 | Gholap | G06K 9/00127 |
| | | | | 382/133 |
| 8,937,653 | B2 * | 1/2015 | Yamada | G02B 21/367 |
| | | | | 348/79 |
| 9,176,310 | B2 * | 11/2015 | Gareau | G02B 21/16 |
| 9,189,678 | B2 | 11/2015 | Tsunomori et al. | |
| 10,628,658 | B2 * | 4/2020 | Bredno | G06K 9/0014 |
| 2005/0136549 | A1 * | 6/2005 | Gholap | G06K 9/0014 |
| | | | | 436/501 |
| 2005/0266395 | A1 * | 12/2005 | Gholap | G06K 9/48 |
| | | | | 435/4 |
| 2006/0014238 | A1 * | 1/2006 | Gholap | G06K 9/0014 |
| | | | | 435/40.5 |
| 2007/0026525 | A1 * | 2/2007 | Marcelpoil | G06T 7/0012 |
| | | | | 436/63 |
| 2010/0279341 | A1 * | 11/2010 | Steiner | G01N 15/1475 |
| | | | | 435/40.5 |
| 2011/0077506 | A1 * | 3/2011 | Driehuys | G01R 33/022 |
| | | | | 600/420 |
| 2011/0111435 | A1 * | 5/2011 | Dobson | G01N 33/566 |
| | | | | 435/7.23 |
| 2012/0115139 | A1 * | 5/2012 | Kuroda | C12Q 1/6886 |
| | | | | 435/6.11 |
| 2013/0030305 | A1 * | 1/2013 | Yu | A61B 5/0084 |
| | | | | 600/476 |
| 2013/0182936 | A1 * | 7/2013 | Yoshihara | G06T 7/11 |
| | | | | 382/133 |
| 2014/0051981 | A1 * | 2/2014 | Schlesinger | A61B 5/03 |
| | | | | 600/420 |
| 2014/0112568 | A1 * | 4/2014 | Liu | G06T 7/0012 |
| | | | | 382/133 |
| 2016/0163043 | A1 | 6/2016 | Mimura et al. | |
| 2016/0275673 | A1 | 9/2016 | Ichitani et al. | |
| 2017/0084021 | A1 * | 3/2017 | Athelogou | G06T 7/0012 |
| 2017/0089896 | A1 * | 3/2017 | Rooney | A61K 51/1027 |
| 2017/0103521 | A1 * | 4/2017 | Chukka | G06T 7/0012 |
| 2017/0262984 | A1 * | 9/2017 | Barnes | G06T 7/0012 |
| 2017/0307496 | A1 * | 10/2017 | Zahniser | G06K 9/0014 |

FOREIGN PATENT DOCUMENTS

| | | |
|---|---|---|
| JP | 2000-321031 | 11/2000 |
| JP | 2006-349533 A | 12/2006 |
| JP | 2011-043350 A | 3/2011 |
| JP | 2013-105245 | 5/2013 |
| JP | 2013-137627 | 7/2013 |
| WO | WO 2015/145643 A1 | 10/2015 |
| WO | WO 2016/076104 A1 | 5/2016 |
| WO | WO 2017/150194 A1 | 9/2017 |

OTHER PUBLICATIONS

European Patent Application No. 17815062.9; Extended Search Report; dated Feb. 21, 2019; 10 pages.

International Search Report issued in parent PCT Application No. PCT/JP2017/018453, dated Aug. 8, 2017.

* cited by examiner

FIG.1
| | PATHOLOGICAL IMAGE | EXTRACTION RESULT |
|---|---|---|
| STAINED WITHOUT UNEVENNESS | 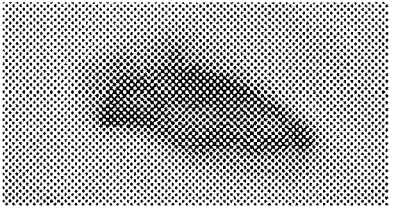 |  |
| STAINED UNEVENLY | 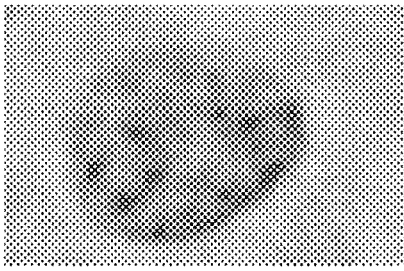 | 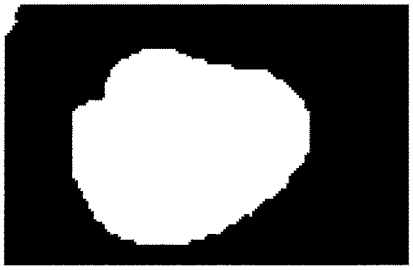 |
| INSIDE UNSTAINED NUCLEUS | 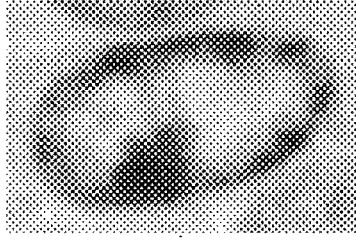 |  |
FIG.2
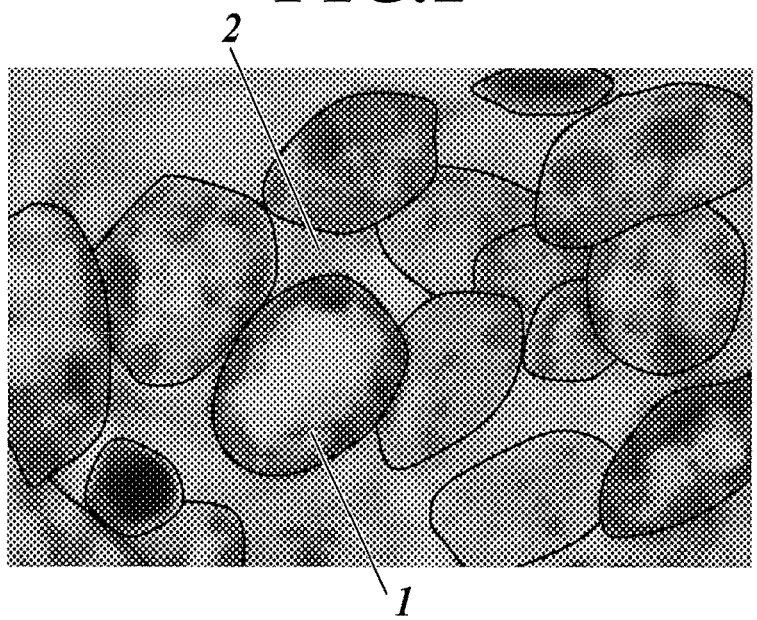

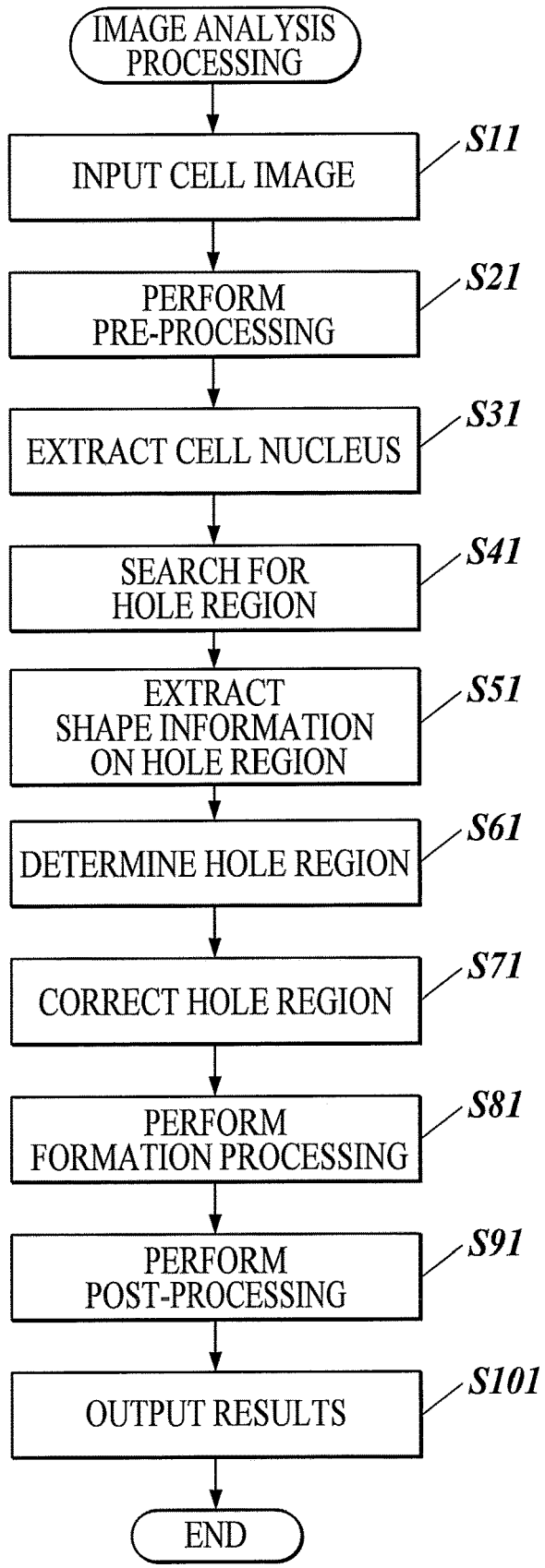

IMAGE PROCESSING DEVICE, IMAGE PROCESSING METHOD, AND RECORDING MEDIUM

The present U.S. Patent Application is U.S. National Phase Application under 35 U.S.C. 371 of International Application PCT/JP2017/018453 filed on May 17, 2017, which claims a priority under the Paris Convention to Japanese Patent Application No. 2016-124037 filed on Jun. 23, 2016, the entire disclosures of which are incorporated herein by reference in their entireties.

TECHNICAL FIELD

The present invention relates to an image processing device, an image processing method, and an image processing program, particularly relates to image processing used in pathological diagnosis.

BACKGROUND ART

Conventionally, in the pathological diagnosis and research in the field of life science, image processing for extracting the shape and number of cells from an image of a tissue specimen has been widely performed. Specifically, for example, after extracting a stained cell nucleus from the image are carried out calculation of a feature amount (such as size and shape) of the extracted structure of the cell nucleus and analysis of expression level or distribution of a specific biological substance (such as cancer protein and gene) in the structure.

When such image processing is visually performed by an observer, it requires a huge amount of labor and the result of the image processing are likely to be largely different depending on the observer. Therefore, in recent years, many techniques have been proposed for performing automatic image processing of an image obtained by photographing a tissue specimen.

However, in an image obtained by photographing an actual tissue specimen, it is rare that all cells are stained uniformly. That is, there are unevenness in staining concentration among cells, staining variation (patchy staining, gradient of staining concentration, etc.) in a cell, an inside-unstained nucleus (a cell nucleus which is stained only in the vicinity of the contour), and the like (see FIG. 1). In addition, when the cells are present at high density, it is more difficult to identify individual cells because multiple cells overlap each other on the image. Since various errors can occur due to such staining unevenness and overlapping in conventional automatic image processing (see FIG. 1), various techniques for correcting the errors have been proposed.

For example, Patent Document 1 discloses a technique capable of extracting individual cells even when multiple cells overlap with each other in an image (see paragraph 0018). Specifically, such a technique is realized by focusing on the staining concentration gradient in each cell and obtaining a sign of an inner product value of a concentration gradient vector at a pixel forming a cell contour and a displacement vector from the pixel to the cell center position (see paragraphs 0027 to 0028, FIG. 10, paragraphs 0084 to 0088, FIGS. 13 to 16, etc. of Patent Document 1).

According to the image processing disclosed in Patent Document 1, it is possible to identify individual cells even when density of cells is high. However, Patent Document 1 does not disclose correction of staining unevenness or unstained inner portion.

Patent Document 2 discloses a technique capable of extracting individual cells even when there is a variation in the staining concentration among cells in the image. Specifically, a binary image is made by changing the threshold value stepwise, a feature amount is calculated for each connected pixel region in the binary image, and only the regions whose feature amount each satisfy a predetermined condition are merged to generate a result image. Thus, even when the threshold value to be used differs from cell to cell, it is possible to detect the object of interest (cell etc.) with high accuracy (see claim 1, paragraph 0009, etc. of Patent Document 2).

According to the technique disclosed in Patent Document 2, it is possible to correct variation in staining concentration among cells (see FIG. 1). However, Patent Document 2 does not disclose correction of staining unevenness in one cell or unstained inner portion.

Patent Document 3 discloses a technique capable of extracting the contour of a cell even when there is color unevenness based on the microstructure or noise inside the cell. Specifically, the outline of cells can be formed as follows: an image obtained by extracting a low frequency component and an image obtained by extracting a high frequency component are generated from an image obtained by photographing cells; an image is generated by filter processing using multiple frequency images different from each other; and threshold processing is performed on the generated image (see claim 1, paragraph 0006, etc. of Patent Document 3). Patent Document 3 also discloses fixing the shape of the cell region(s) by fill-up processing of a blank and the like on the image after the threshold processing (see paragraph 0059, etc.).

CITATION LIST

Patent Literature

[Patent Document 1] Japanese Patent Application Laid Open Publication No. 2000-321031
[Patent Document 2] Japanese Patent Application Laid Open Publication No. 2013-105245
[Patent Document 3] Japanese Patent Application Laid Open Publication No. 2013-137627

SUMMARY OF INVENTION

To achieve at least one of the abovementioned objects, according to an aspect of the present invention, an image processing device may comprise: an input receiver of inputting an image obtained by photographing a specimen subjected to staining; and a hardware processor that: extracts a region subjected to the staining from the image as a cell region; extracts a region as a candidate region, the region being surrounded by the cell region and not being subjected to the staining; extracts a feature amount of the candidate region; determines whether or not the candidate region is a cell region on a basis of the feature amount; and corrects the candidate region which is determined to be a cell region by the distinction means to be a cell region.

In another aspect of the present invention, a non-transitory computer readable medium storing an image processing program may cause a computer to extract a region subjected to the staining from the image as a cell region; extract a region as a candidate region, the region being surrounded by the cell region and not being subjected to the staining; extract a feature amount of the candidate region; determine whether or not the candidate region is a cell region on a basis of the feature amount; and correct the candidate region which is determined to be a cell region to be a cell region.

According to Patent Documents 1 to 3, it is possible to reduce errors to some extent, which are due to overlapping of cells, staining unevenness, and unstained inner portion in an image obtained by photographing a tissue specimen. However, as shown in FIG. 2, for example, an inside-unstained nucleus 1 and a background 2 (a region where no cells exist in the image) surrounded by multiple cell nuclei cannot be distinguished from each other if they are both present in a cell image. As a result, the background 2 surrounded by multiple cell nuclei may be regarded as an unstained inner portion of a nucleus and subjected to filling processing of a blank or, alternatively, the inside-unstained nucleus 1 may be regarded as a background surrounded by multiple cell nuclei, and subjected to a dividing process. This results in problems of errors caused in the analysis results.

The main object of the present invention is to provide an image processing device, an image processing method, and an image processing program in which a background surrounded by multiple cell nuclei and an inside-unstained nucleus can be distinguished from each other in image processing for extracting stained cells from an image obtained by photographing a tissue specimen.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 1 is a diagram showing pathological images of cells with different staining conditions and extraction results of cell nucleus by conventional image processing.

FIG. 2 is a diagram showing an example of a cell image.

FIG. 5 is a flowchart showing image analysis processing of a first embodiment.

DESCRIPTION OF EMBODIMENTS

Advantageous Effects of the Invention

According to the image processing device, the image processing method, and the image processing program of the present invention, it is possible to distinguish a small background surrounded by multiple cell nuclei and an inside-unstained nucleus from each other in image processing for extracting stained cells from an image obtained by photographing a tissue specimen.

Hereinafter, one or more embodiments of the present invention will be described with reference to the drawings. However, the scope of the invention is not limited to the disclosed embodiments.

<Configuration of Pathological Diagnosis Support System 100>

Figure 3:
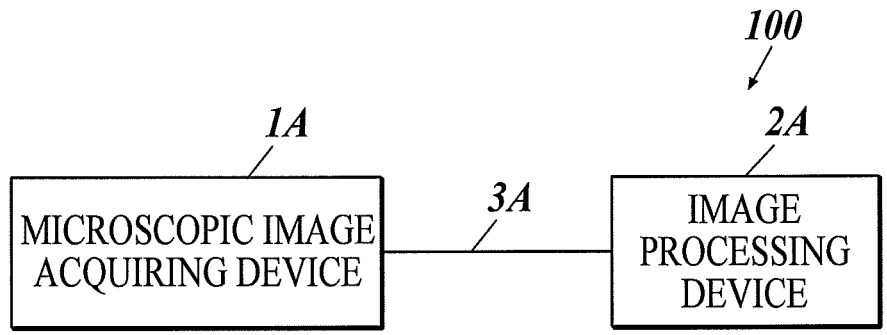
FIG. 3 is a diagram showing a system configuration of diagnosis support information generation system of the present invention.

FIG. 3 shows an overall configuration example of a pathological diagnosis support system 100.

The pathological diagnosis support system 100 acquires a microscopic image of a tissue section of a human body stained with a predetermined staining reagent and analyzes the acquired microscopic image. The system outputs a feature amount(s) which quantitatively represents expressions of a specific biological substance in the tissue section of the observation target.

As shown in FIG. 3, the pathological diagnosis support system 100 is configured such that the microscopic image acquiring device 1A and the image processing device 2A are connected so as to be able to send and receive data via an interface, such as a cable 3A.

The connection between the microscopic image acquiring device 1A and the image processing device 2A is not particularly limited. For example, the microscopic image acquiring device 1A and the image processing device 2A may be connected via a LAN (Local Area Network) or may be connected wirelessly.

The microscopic image acquiring device 1A is a well-known microscope with a camera which obtains the microscopic image of the tissue section on a slide placed on a slide fixing stage and sends it to the image processing device 2A.

The microscopic image acquiring device 1A includes an irradiating unit, an image forming unit, an imaging unit, a communication I/F, and the like. The irradiating unit includes a light source, a filter, and the like, and irradiates the tissue section on the slide placed on the slide fixing stage with light. The image forming unit includes an ocular lens, an object lens, and the like, and forms an image of transmitted light, reflected light, or fluorescence from the tissue section on the slide due to the irradiated light. The imaging unit is a camera provided in a microscope which includes a CCD (Charge Coupled Device) sensor and the like, and captures an image on an image forming face formed by the image forming unit to generate digital image data of the microscopic image. The communication I/F sends the image data of the generated microscopic image to the image processing device 2A.

The microscopic image acquiring device 1A includes a bright field unit in which the irradiating unit and the image forming unit suitable for bright field observation are combined. The microscopic image acquiring device 1A may further include a fluorescent unit in which the irradiating unit and the image forming unit suitable for fluorescence observation are combined.

The microscopic image acquiring device 1A is not limited to a microscope having a camera. For example, a virtual microscope slide creating device which scans a slide on a slide fixing stage of a microscope and obtains a microscopic image of the entire tissue section may be used (for example, see Japanese Patent Application Laid-Open Publication No. 2002-514319). According to the virtual microscope slide creating device, image data can be obtained with which the entire image of the tissue section on the slide can be viewed at once on a display.

The image processing device 2A analyzes the microscopic image received from the microscopic image acquiring device 1A to calculate distributions of specific biological substances in the tissue section of the observation target.

Figure 4:
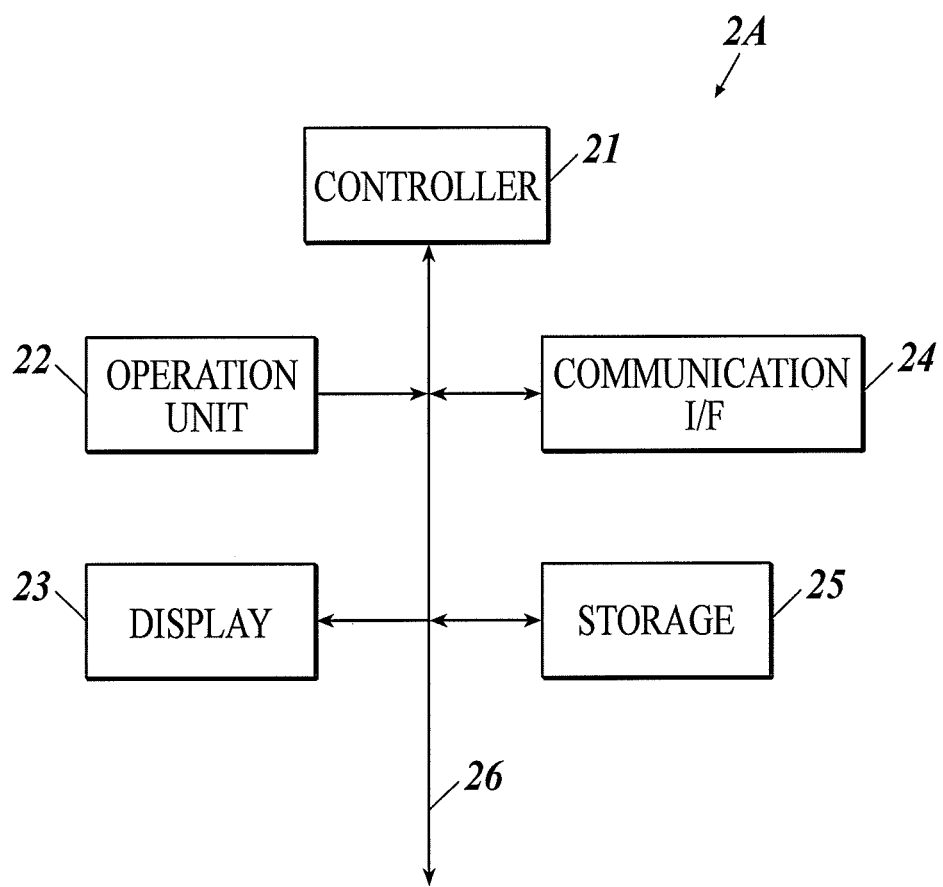
FIG. 4 is a block diagram showing a functional configuration of an image processing device of the present invention.

FIG. 4 shows an example of a functional configuration of the image processing device 2A.

As shown in FIG. 4, the image processing device 2A includes a controller 21, an operation unit 22, a display 23, a communication I/F 24, a storage 25, and the like, and each unit is connected through a bus 26.

The controller 21 includes a CPU (Central Processing Unit), a RAM (Random Access Memory), and the like, performs various processing in coordination with various programs stored in the storage 25, and collectively controls the operation of the image processing device 2A.

For example, the controller 21 performs image analysis processing in coordination with programs stored in the storage 25, and realizes functions as a cell region extractor, a candidate region extractor, a feature amount extractor, a distinction means, a threshold setter, and a corrector.

The operation unit 22 includes a keyboard provided with character input keys, numeric input keys, and various function keys and a pointing device such as a mouse, and outputs depression signals of the pressed keys of the keyboard and operation signals of the mouse as the input signal to the controller 21.

The display 23 includes, for example, a monitor such as a CRT (Cathode Ray Tube), an LCD (Liquid Crystal Display), and the like, and displays various screens according to an instruction of a display signal input from the controller 21.

The communication I/F 24 is an interface for sending and receiving data to and from external devices such as the microscopic image acquiring device 1A. The communication I/F 24 realizes a function as the input receiver of a cell image.

The storage 25 includes, for example, an HDD (Hard Disk Drive), a nonvolatile semiconductor memory, and the like. The storage 25 stores various programs and various pieces of data as described above.

Other than the above, the image processing device 2A may include a LAN adaptor, a router, and the like, and may be connected to external devices through a communication network such as a LAN.

<Images>

In the present embodiment, the image processing device 2A preferably analyzes a cell image representing shapes of stained cells.

The cell image is, for example, a microscopic image acquired by, in the microscopic image acquiring device 1A, forming and capturing an enlarged image of a tissue section stained with any reagent which can stain a specific structure in cell(s) (for example, a cell nucleus, a cell membrane, and the like), such as a reagent for hematoxylin staining (an H-staining reagent) or a reagent for hematoxylin-eosin staining (an HE-staining reagent) with a bright field. The bright field image represents morphology of cell in the tissue section. Hematoxylin (H) is a bluish violet dye and stains a cell nucleus, bony tissue, a portion of cartilaginous tissue, serous components, and the like (basophilic tissue and the like). Eosin is a red to pink dye and stains cytoplasm, connective tissue of soft tissue, a red blood cell, fibrin, endocrine granules and the like (acidophilic tissue and the like).

Examples of the cell image may include, other than the bright field image, a fluorescent image obtained by capturing fluorescence emitted from a fluorescent staining reagent which is used for staining a tissue section and which can specifically stain a specific structure in cells. Examples of the fluorescent staining reagent used for obtaining the cell image include DAPI staining reagent for staining cell nuclei, Papanicolaou staining reagent for staining cytoplasm, and the like.

<Operation of Pathological Diagnosis Support System 100 (Including Image Processing Method)>

Hereinafter, specific embodiments are described regarding an operation of obtaining the cell image showing a morphology of cells and extracting stained structures in the pathological diagnosis support system 100. In the present embodiment, region of a cell nucleus (cell nuclei) stained through the H-staining is extracted from a microscopic image obtained by photographing a tissue specimen collected from a human body, but the present invention is not limited thereto.

First, the operator stains a tissue section by a known method using the H-staining reagent.

After the staining, a cell image is obtained with the microscopic image acquiring device 1A as in the following procedures (a1) to (a3).

(a1) The operator mounts a tissue section in which cell nuclei have been stained with the H-staining reagent on a slide, and places the slide on a slide fixing stage of the microscopic image acquiring device 1A.

(a2) The bright field unit is set, the capturing magnification and focus are adjusted, and the observation target region in the tissue section is positioned in the visual field.

(a3) Capturing is performed with the imaging unit to generate image data of a cell image and the image data is sent to the image processing device 2A.

Hereinafter, image processing of the cell image sent to the image processing device 2A is described in detail.

First Embodiment

FIG. 5 shows a flowchart of the image processing performed in the image processing device 2A. The image processing shown in FIG. 5 is performed by the controller 21 in coordination with the image processing program stored in the storage 25. The controller 21 performs the following processing in accordance with the program for image processing.

Figure 6A:
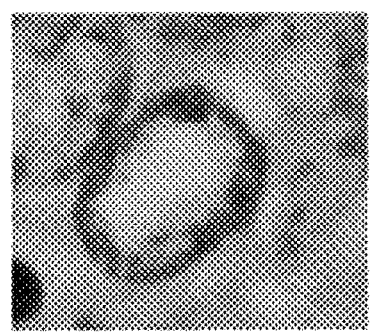
FIG. 6A is an example of a cell image.

First, when a cell image (FIG. 6A) is input from the microscopic image acquiring device 1A through the communication I/F 24 (step S11: input step), the controller 21 performs optional pre-processing of the cell image (step S21). The pre-treatment includes, for example, processing using Gaussian filter or closing processing to remove noise components in the image.

Figure 6B:
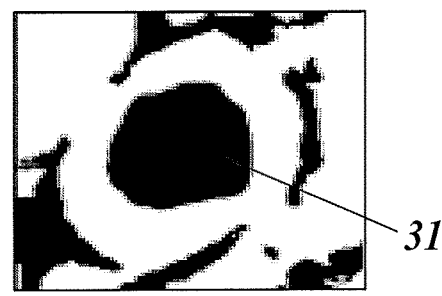
FIG. 6B is an example of a stained image.
Figure 7A:
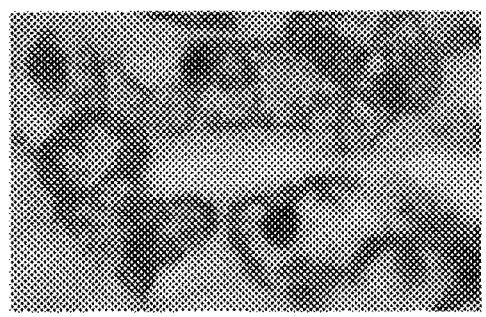
FIG. 7A is an example of a cell image.
Figure 7B:
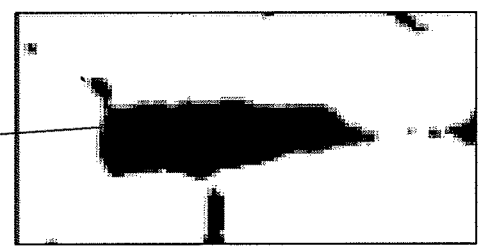
FIG. 7B is an example of a stained image.
Figure 8:
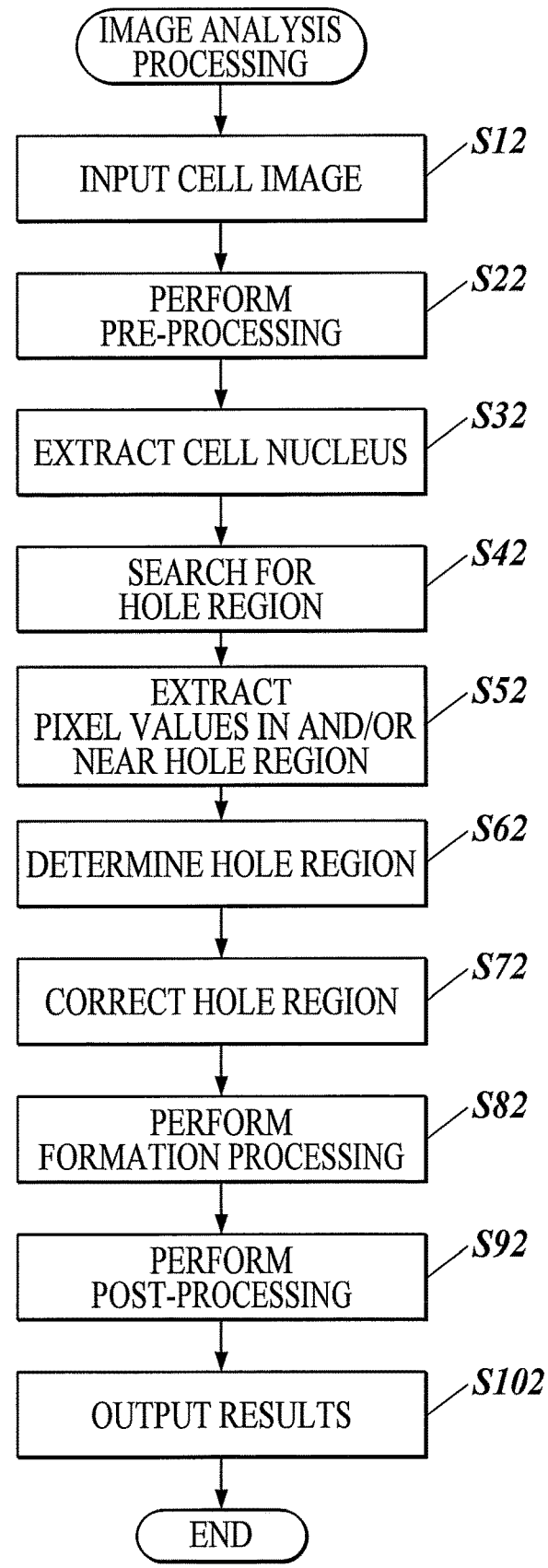
FIG. 8 is a flowchart showing image analysis processing of a second embodiment.
Figure 9:
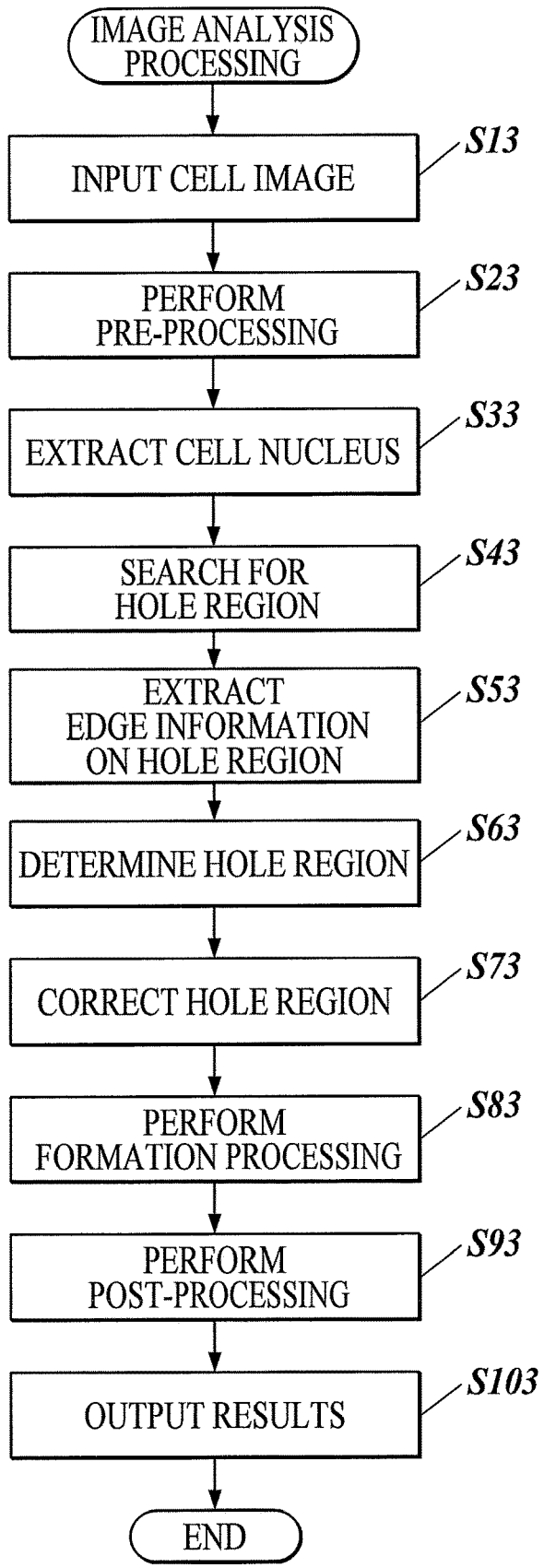
FIG. 9 is a flowchart showing image analysis processing of a third embodiment.

Subsequently, the controller 21 extracts a region(s) (stained region(s)) stained in blue by H staining from the cell image after the pre-processing to generate a binary image (stained image) (step S31: stained region extraction step). FIG. 6B and FIG. 7B show examples of stained images respectively generated from the cell images of FIG. 6A and FIG. 7A. Stained regions and unstained regions are represented by white and black, respectively.

In the stained region extraction step (step S31), for example, the cell image is subjected to color decomposition for extraction of blue components and conversion to a monochrome image. Subsequently, a stained image is generated by binarizing each pixel value by threshold processing using a predetermined threshold value.

An optional noise processing may be performed with the binary image obtained in the stained region extraction step (step S31). For example, small region corresponding to a noise etc. can be removed by closing processing of the binary image. The closing processing includes performing dilation processing and then erosion processing by the same number of times. The dilation processing is processing of replacing a target pixel with a white pixel when any of the pixels within the range of n×n pixels (n is an integer of 2 or more) from the target pixel is white. The erosion processing is processing of replacing the target pixel with a black pixel when any of the pixels within the range of n×n pixels from the target pixel is black.

Subsequently, the controller 21 searches the stained image generated in the stained region extraction step (step S31) for a hole region(s) (step S41: hole region search step).

In the present embodiment, the "hole region" is an unstained region surrounded by the stained region(s) and refers to a candidate region of a cell nucleus, rather than a background. The unstained region(s) surrounded by stained regions and having a size (such as an area and a major diameter) larger than a predetermined value may be determined to be an unstained region which is not the hole region, since such region(s) clearly does not represent an unstained inner portion of cell nucleus. The extracted hole region(s) is respectively subjected to labelling processing. In the stained images of FIGS. 6B and 7B are respectively shown hole regions 31 and 32 surrounded by a stained region represented in white.

Subsequently, the controller 21 extracts feature amount(s) of the hole region (step S51: feature amount extraction step) and determines whether the hole region is an unstained inner portion of a cell nucleus or a background on the basis of the feature amount (step S61: distinction step). Table 1 shows summary of major feature amounts (classification and type) used in the present invention and the relations between the feature amounts and the distinction results.

TABLE 1

| Classification | Feature amount | Background surrounded by cell nuclei | Unstained inner portion of cell nucleus |
| --- | --- | --- | --- |
| Shape | Circularity | Low | High |
|  | Area | Large | Small |
|  | Convex hull rate | Low | High |
|  | Number of convex portions | Many | Few |
| Pixel value | Inside of hole | High | Low |
|  | Periphery | Large variation | Small variation |
| Edge | Intensity | Strong | Weak |
|  | Direction | Large variation | Small variation |
|  | Curvature | Center directions are varied. | Center directions are the same. |
| Machine learning | Score | High background score | High cell nuclear score |

In the feature amount extraction step (Step S51) of the first embodiment, feature amount(s) regarding shapes of the hole region is calculated. The feature amount preferably includes at least one of circularity, area, convex hull rate, and number of convex portions of the hole region. Any method may be used for calculating a feature amount. Specific examples of the method are as follows.

The circularity can be obtained by the expression of $4\pi S/L^2$, where S is the area and L is the circumferential length of the hole region. The convex hull rate is the ratio of the area of the hole region to the area of the convex hull polygon including the hole region. Each of the circularity and the convex hull rate takes a value between 0 and 1, and the value closer to 1 means that the shape is closer to a circular shape.

In the calculation of the number of convex portions, first, the coordinate of each pixel on the outline of the hole region is converted into a polar coordinate with the center of gravity of the hole region taken as the origin, and a distance is calculated from each point on the outline of the hole region to the origin. Subsequently, the number of times the distances along the outline of the hole region increases or decreases is calculated and determined to be the number of convex portions. Before the polar coordinate conversion, smoothing processing may be of the stained image may be performed by any known method.

Subsequently, the controller 21 compares the feature amount extracted in step S51 with a preset threshold value to determine whether the hole region is an unstained inner portion of the nucleus or a background surrounded by multiple cell nuclei, for example, on the basis of the following criteria (step S61: distinction step).

When the hole region indicates an unstained inner portion of a nucleus, its area is smaller than a cell nucleus. On the other hand, if the hole region is a background surrounded by multiple cell nuclei, its area may be larger than a cell nucleus. Therefore, when the area of the hole region is larger than a predetermined threshold value (for example, the area of a standard cell nucleus), the hole region is determined to be a background. When the area of the hole region is smaller than the predetermined threshold value, it may be determined to be an unstained inner portion of a nucleus. The distinction may be further made using feature amount(s) other than the area.

Further, when the hole region indicates an unstained inner portion of a nucleus, its shape is often close to a circular shape, as the hole region 31 in FIG. 6B. On the other hand, when the hole region is a background surrounded by multiple cell nuclei, as the hole region 32 in FIG. 7B, its shape is highly likely to be distorted. Therefore, when the circularity is larger than the predetermined threshold value or when the convex hull rate is larger than a predetermined threshold value and/or the number of convex portions is less than a predetermined number, the hole region is determined to be an unstained inner portion of a nucleus.

For performing efficient distinction, preferably, the image processing method of the present invention further includes a threshold setting step of setting a threshold value used in the distinction step (step S61) according to the specimen. The threshold setting step may be performed at any timing prior to the distinction step (step S61).

In the threshold setting step, the threshold value is preferably set on the basis of at least one of the cancer type, the progression of the cancer, the method of collecting the tissue, and the staining method regarding the specimen to be observed.

Such information is input in advance via the operation unit 22 or a communication I/F 24, for example.

It is known that the probability that the hole region is an unstained inner portion of a nucleus (or the probability that the hole region is a background surrounded by multiple cell nuclei) is different depending on the above information as follows.

For example, the area of a cell and the occurrence probability of an unstained inner portion in a cell are different depending on the type of cancer. Further, even when the cancer types are the same, the occurrence probability of an unstained inner portion may be different depending on the progression of cancer. In general, it is known that the unstained inner portion is more likely to occur as the cancer progresses.

Even for specimens prepared from the same breast cancer tissue, it is known that the density of cells is high in a specimen collected by needle biopsy, and the density of cells in a section sliced from tissue is low. As the lower the density of cells, the lower the probability that cells overlap in the cell image. Therefore, a background surrounded by multiple cell nuclei is unlikely to be present, and the hole region is likely to be an unstained inner portion of an inside-unstained nucleus.

As for a specimen in which an unstained inner portion is likely to occur, in the threshold setting step, the threshold value of the feature amount used in the distinction step (step S61) is set to a value so that the hole region is readily determined to be an unstained inner portion of an inside-unstained nucleus. Specifically, for example, when an area is used as the feature amount, a large threshold value is set.

Figure 6C:
FIG. 6C is an example of a corrected image.

Subsequently, the controller 21 corrects the stained image on the basis of the distinction result to generate a corrected image (step S71: correction step). Specifically, in the correction processing, by binarization processing to fill the unstained inner portion of an inside-unstained nucleus (unstained region), an image of a cell nucleus region including the filled hole region and the stained region(s) is obtained. More specifically, in the correction step (step S71), the hole region 31 determined to be an unstained inner portion is changed to white in the stained image shown in FIG. 6B, and a corrected image shown in FIG. 6C is obtained.

Subsequently, the controller 21 performs formation processing for extracting individual cell nuclei (nucleus) from the corrected image (step S81). In the formation processing, division processing, integration processing, and the like of the cell nucleus region in the corrected image are performed by any known method of extracting the shape of the individual cell nuclei.

Subsequently, the controller 21 performs post-processing including analysis of the feature amount of the cell nucleus and the like for diagnostic information generation (step S91), and outputs an analysis result (step S101).

Second Embodiment

Next, image processing according to the second embodiment will now be described.

FIG. 5 shows a flowchart of the image analysis processing performed in the image processing device 2A. The image analysis processing shown in FIG. 5 is performed by the controller 21 in coordination with the image processing program stored in the storage 25. The controller 21 performs the following processing in accordance with the image processing program.

The processing in steps S12 to S42 and S72 to S102 in the second embodiment is performed in the same way as the processing in steps S11 to S41 and S71 to S101 in the first embodiment. The following descriptions will be mainly for configurations different from those according to the above first embodiment, and descriptions for configurations common to those of the first embodiment will be omitted.

In the feature amount extraction step of the second embodiment (step S52), a feature amount(s) based on pixel values of the pixels in the inside and/or periphery of the hole region in the cell image is calculated. The pixels in the "periphery" of the hole region are defined as pixels outside of the hole region and at a position within a predetermined distance from the hole region. The predetermined distance is appropriately set according to the type of cells, area of the hole region, and the like.

In the present embodiment, the value of saturation (S) calculated from the RGB values of each pixel in the cell image is preferably used as the pixel value, as the feature amount representing the concentration of the H staining. The darker the cell nucleus is stained by H staining, the higher pixel value of S is calculated.

Other examples of the pixel value include the value of a color component appropriately selected according to the type of staining, the brightness of each pixel in the monochrome image obtained by gray scale conversion of the cell image, or the like.

The feature amount calculated on the basis of the pixel value may be, for example, a pixel value (for example, an average value) in the hole region, a variation (for example, a variation coefficient) of pixel values of the periphery of the hole region, difference between average values of pixel values in the inside and the periphery of the hole region, and the like.

In the distinction step of the second embodiment (step S62), the feature amount extracted in step S52 is compared with a preset threshold value to determine whether the hole region is an unstained inner portion of the nucleus or a background surrounded by multiple cell nuclei, for example, on the basis of the following criteria.

In the cell image obtained by photographing a specimen subjected to H-staining, it is conventionally known that, if the color in the hole region indicating the unstained inner portion of a nucleus (see FIG. 6A) and the color in the hole region indicating a background surrounded by multiple cell nuclei (see FIG. 7B), the color in the hole region indicating the background is lighter. Accordingly, if the average of pixel values in the hole region is smaller than a predetermined threshold value (closer to white), the hole region is determined to be a background surrounded by multiple cells.

When the hole region indicates an unstained inner portion of a nucleus, the stained region surrounding each hole region corresponds to a single cell nucleus. Therefore, the periphery of the hole region is likely to be stained relatively uniformly. On the other hand, when the hole region indicates a background region surrounded by multiple cell nuclei, the staining concentrations are likely to be different from each other for the multiple cells surrounding the hole region. Accordingly, if the variation of the pixel values in the periphery of the hole region is larger than a predetermined threshold value, the hole region is determined to be a background surrounded by multiple cell nuclei.

Third Embodiment

Next, image processing according to the third embodiment will now be described.

The processing in steps S13 to S43 and S73 to S103 in the third embodiment is performed in the same way as the processing in steps S11 to S41 and S71 to S101 in the first embodiment. The following descriptions will be mainly for configurations different from those according to the above-described first embodiment. The descriptions for configurations common to those of the first embodiment will be omitted.

In the feature amount extraction step of the third embodiment (step S53), a feature amount(s) based on edges of the hole region is calculated. Subsequently, in the distinction step (step S63), the feature amount extracted in step S53 is compared with a preset threshold value to determine whether the hole region is an unstained inner portion of the nucleus or a background surrounded by multiple cell nuclei, for example, on the basis of the following criteria.

(1) Feature Amount Regarding Edge Intensity

The edge intensity in the present embodiment means an amount of color change at an edge portion of a region corresponding to the hole region in the cell image and is calculated by a known method. As the feature amount regarding the edge intensity, for example, the average value of the edge intensity of each hole region is calculated. The clearer the outline is, the higher the edge intensity is.

When the hole region indicates an unstained inner portion of a nucleus, since the inside and the outside of the hole region are not divided by a nuclear membrane and the like, the edge intensity is weak in many cases. On the other hand, when the hole region indicates a background surrounded by multiple cell nuclei, since the nuclear membranes of the surrounding cell nuclei form the edge of the hole region, it is highly possible that the edge intensity is stronger than that of an unstained inner portion of a nucleus. Therefore, when the edge intensity is larger than a predetermined threshold value, it is determined in the distinction step (step S63) that the hole region indicates an unstained inner portion of a nucleus.

(2) Feature Amount with Respect to Edge Normal Direction

Figure 10A:
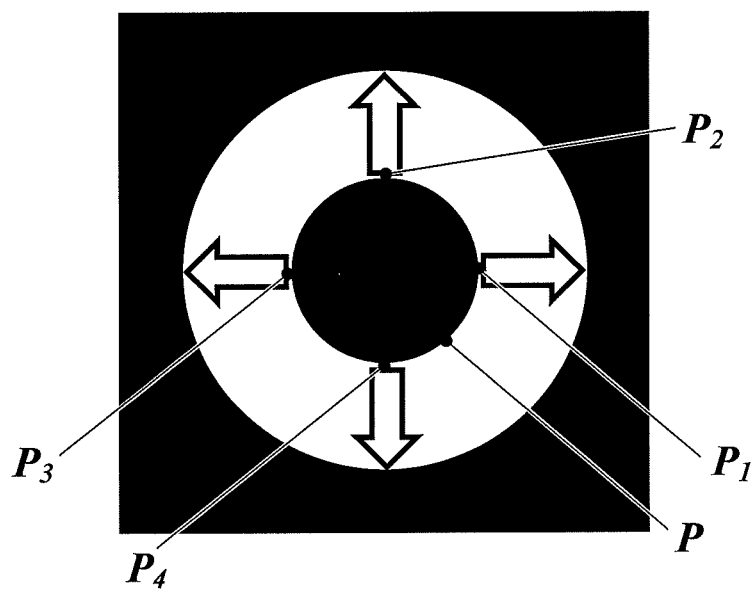
FIG. 10A is a schematic diagram of a stained image showing an inside-unstained nucleus.
Figure 10B:
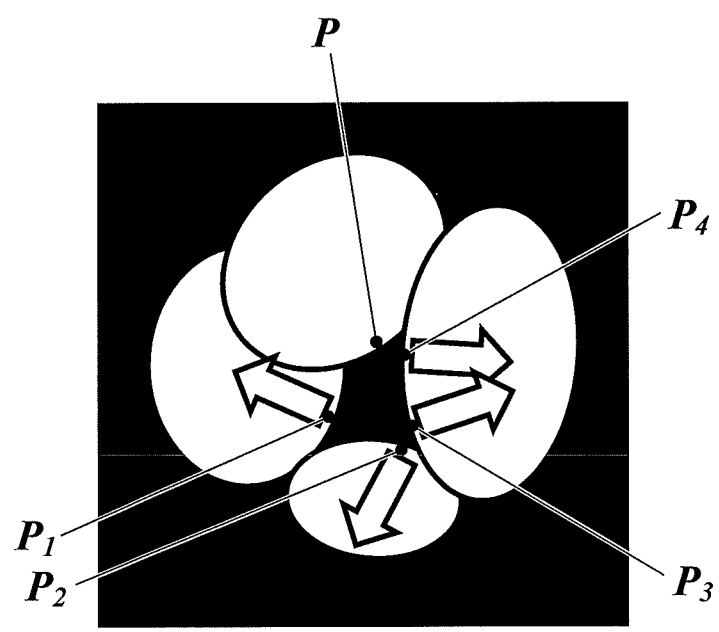
FIG. 10B is a schematic diagram of a stained image showing an background surrounded by multiple cell nuclei.
Figure 11:
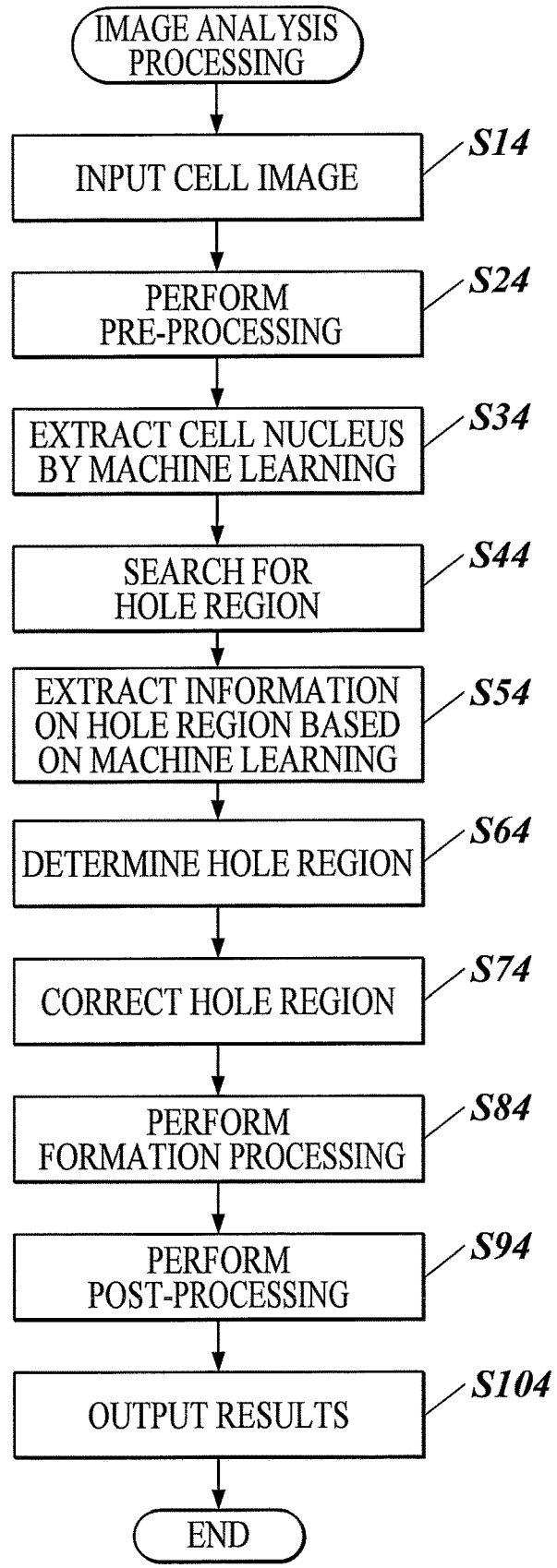
FIG. 11 is a flowchart showing image analysis processing of a fourth embodiment.

The "edge normal direction" in the present embodiment is a normal direction of a tangent at the edge portion of the hole region and a direction from the inside to the outside of the hole region. FIGS. 10A and 10B are schematic diagrams of a stained image showing an inside-unstained nucleus and a background surrounded by multiple cell nuclei. As an example of the feature amount with respect to the edge normal direction, an arbitrary starting point P (see FIGS. 10A and 10B) is set on the edge, and the correlation coefficient of 'the distance from the starting point (the length along the edge)' and 'the amount of change in edge direction, with the edge direction of the starting point is used as a reference' is calculated for multiple points on the edge (for example, P1 to P4 in FIGS. 10A and 10B). For example, in the case where the hole region is substantially circular as shown in FIG. 10A, since the edge normal direction (the direction indicated by an arrow) changes smoothly along the edge, the correlation is high between the distance from the starting point P and the edge normal direction. On the other hand, in the case where the hole region is distorted as shown in FIG. 10B, since the edge normal direction (the direction indicated by an arrow) suddenly changes at the corner portion of the edge, the correlation is low between the distance from the starting point P and the edge normal direction (for example, see between P2 and P3 in FIG. 10B).

When the hole region indicates an unstained inner portion of a nucleus, as shown in FIG. 6B, its shape is relatively circular in many cases. On the other hand, when the hole region is a background surrounded by multiple cell nuclei, as shown in FIG. 7B, it is highly possible that it has a distorted shape. Therefore, when the correlation coefficient in the edge normal direction is higher than a predetermined threshold value, it is determined that the hole region indicates an unstained inner portion of a nucleus.

(3) Feature Amount with Respect to Curvature

The "curvature" in the present embodiment indicates the degree of local bending at the edge. An example of the feature amount with respect to the curvature is obtained by, for example, calculating a variation in center coordinate position of a curvature circle which is each obtained by approximation of a part of an edge, for each edge of the hole region divided into a predetermined number. The closer the shape of the hole region is to a circle, the smaller the variation in the center coordinate position of the curvature circles is.

When the hole region indicates an unstained inner portion of a nucleus, as shown in FIG. 6B, its shape is relatively circular in many cases. On the other hand, when the hole region is a background surrounded by multiple cell nuclei, as shown in FIG. 7B, it is highly possible that it has a distorted shape. Therefore, when the variation in curvature is smaller than a predetermined threshold value, it is determined that the hole region indicates an unstained inner portion of a nucleus.

Fourth Embodiment

Next, image processing according to the fourth embodiment will now be described.

The processing in steps S14 to S24, S44, and S74 to S104 in the fourth embodiment is performed in the same way as the processing in steps S11 to S21, S41, and S71 to S101 in the first embodiment. The following descriptions will be mainly for configurations different from those according to the above first embodiment, and descriptions for configurations common to those of the first embodiment will be omitted.

In the stained region extraction step in the fourth embodiment, on the basis of the result of machine learning, a binary image (stained image) is generated from the cell image after the pre-processing. In the binary image, a region(s) (stained region(s)) subjected to H staining is extracted. Any known machine learning may be used, such as Deep Learning, SVM (Support Vector Machine), or the like.

In the feature amount extraction step (step S54) in the fourth embodiment, the feature amount based on machine translation is calculated. Any known machine learning may be used, such as Deep Learning, SVM (Support Vector Machine), or the like. Examples of the used feature amount include a nuclear score representing likeness of cell nucleus, a background score representing likeness of a background, an edge score representing likeness of an edge, and the like.

Figure 12A:
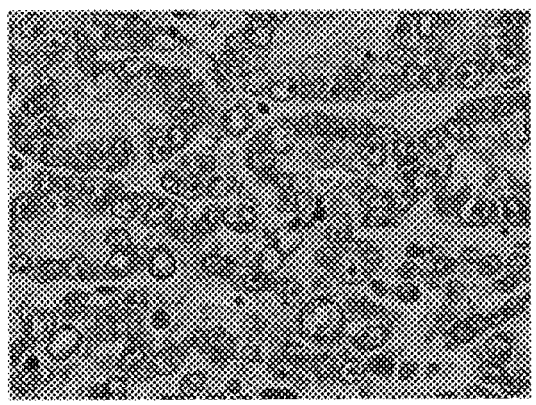
FIG. 12A is an example of a cell image.
Figure 12B:
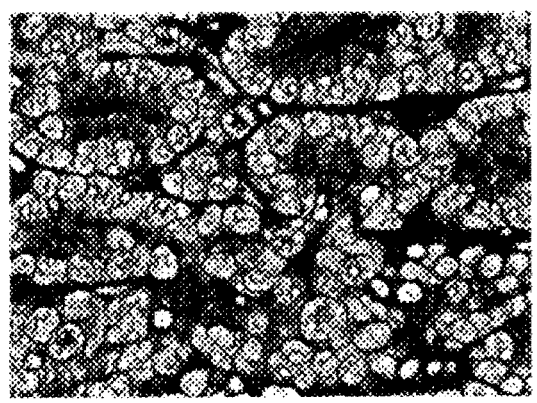
FIG. 12B is an example of a nuclear score image.
Figure 12C:
FIG. 12C is an example of a background score image.
Figure 12D:
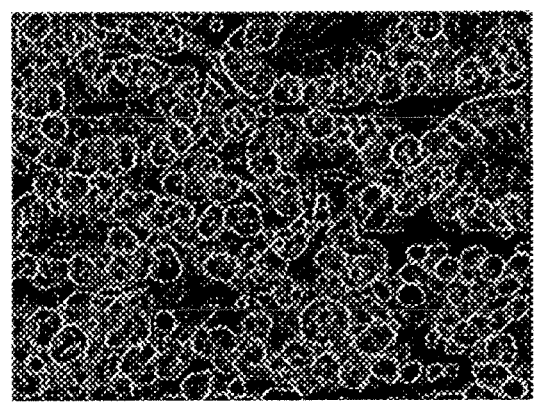
FIG. 12D is an example of an edge score image.

In FIGS. 12B to 12D, examples of images showing nuclear scores, background scores, and edge scores calculated from the cell image in FIG. 12A. Pixels of high score is represented in white.

In the distinction step (step S64) in the fourth distinction method, by comparing the feature amount(s) extracted in the feature amount extraction step (step S54) and the threshold value set in advance, it is determined whether the hole region is an unstained inner portion of nucleus or a background surrounded by multiple cell nuclei.

Hereinafter, image processing in steps S34 to S64 are described with reference to the drawings.

Figure 13A:
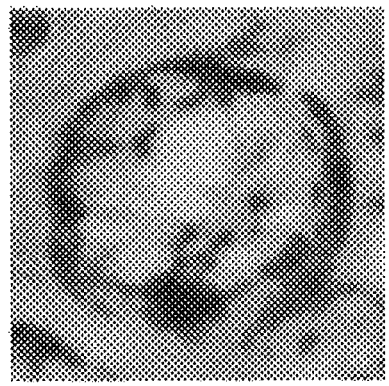
FIG. 13A is an example of a cell image.
Figure 13B:
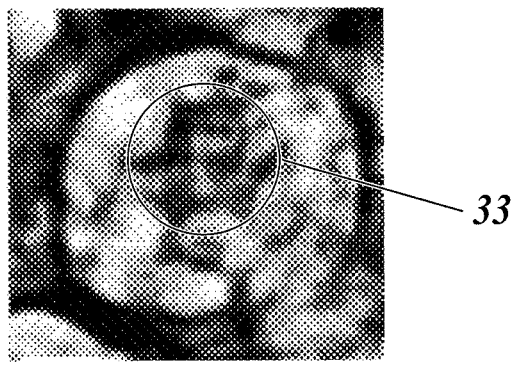
FIG. 13B is an example of a nuclear score image.
Figure 13C:
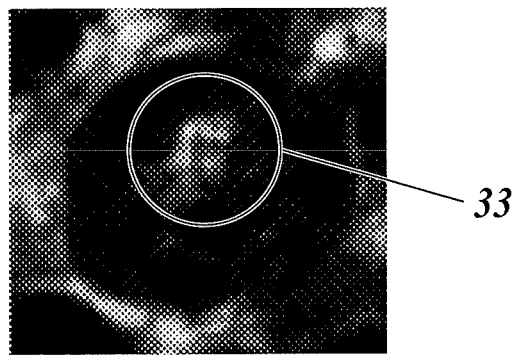
FIG. 13C is an example of a background score image.

FIG. 13A is an example of a cell image obtained by photographing an inside-unstained nucleus. FIGS. 13B and 13C show an example of a nuclear score image and an example of a stained image and a background score image. In step S34 in the fourth embodiment, threshold processing is performed on the nuclear score image of FIG. 13B for extracting a portion having a nuclear score higher than a predetermined threshold value and likely to be a stained region (a region having a color close to white in FIG. 13B) as a cell nucleus region. A stained image is thereby created.

The subsequent hole region search step (step S44) is performed in the same way as step S41 in the first embodiment.

Subsequently, in the feature amount extraction step (step S54), background scores are extracted to obtain a background image. FIGS. 13B and 13C each show a hole region 33 extracted in step S33. Since the background score of a portion corresponding to the hole region 33 is low according to FIG. 13C, the hole region is determined to be an unstained inner portion of a nucleus (step S64: distinction step). In the distinction step, the background score of a portion corresponding to the hole region is compared with a preset threshold value and when the background score is less than the threshold, the hole region is determined to be an unstained inner portion of a nucleus.

If, for example, the background score is larger than the threshold value while a nuclear score in the hole region is small as described above, the hole region 33 is considered to be a background surrounded by multiple cell nuclei.

The distinction accuracy may be further improved by using a score (for example, an edge score) other than the score with respect to the likeness of a cell nucleus and a background as the distinction targets.

In the feature amount extraction step (step S54), if multiple types of scores (for example, a background score and an edge score) are used as the feature amount, a final distinction may be made using any predetermined method of weighing results of relationship between the background score and the threshold and the relationship between the edge score and the threshold.

According to the embodiment of the present invention described above, it is possible to fill the hole region corresponding to an unstained inner portion of nucleus only, without erroneous filling of the background. Thus, it is possible to enhance the extraction accuracy of the cell nucleus. The diagnostic accuracy can be improved by the pathological diagnosis using the image processing of the present invention, so that a more detailed treatment plan is made.

It should be noted that the descriptions in the above embodiments are preferable examples of the present invention, and the present invention is not limited thereto.

For example, in the distinction step, the hole region may be determined to be not only whether an unstained inner portion of a nucleus or a background surrounded by multiple cell nuclei, but whether an unstained inner portion of a nucleus, a background surrounded by multiple cell nuclei, or incapable of being determined automatically. An operator determines the hole region which is determined to be incapable of being determined automatically to be an unstained inner portion of nucleus or a background surrounded by multiple cell nuclei on the basis of the cell image or the like displayed on the display 23, and inputs the distinction result via the operation unit 22, for example.

Further, the feature amounts extracted in the feature amount extraction step and the distinction methods described in the first to fourth embodiments may be used in combination.

Specifically, for example, the distinction based on the area of the hole region according to the first embodiment and the distinction using the score based on machine learning according to the fourth embodiment may be independently performed, and final distinction may be made by weighting each distinction result. In addition, if it is determined that the hole region is incapable of being determined automatically according to one embodiment, the distinction may be made using the method according to another embodiment.

In the above embodiments, the cell nucleus is extracted from the image obtained by photographing the tissue section subjected to H-staining on the basis of the staining, but the staining method is not limited thereto, and, other than the cell nucleus, any structure can be extracted, such as a cell membrane. Further, an image obtained by photographing any tissue specimen, such as cultured cells and a specimen collected by needle biopsy, may be used as the cell image.

In addition, in the above description, examples of using HDD, a semiconductor nonvolatile memory or the like as a computer readable medium for the program according to the present invention have been disclosed, but the medium is not limited to these examples. For other computer readable media, it is possible to apply a portable recording medium, such as CD-ROM. Moreover, as a medium that provides data of the program according to the present invention via a communication line, a carrier wave may be applied.

Besides, detailed configurations and operations of each device constituting the pathological diagnosis support system 100 can also be appropriately modified within a range that does not depart from the spirit of the present invention.

Although embodiments of the present invention have been described and illustrated in detail, the disclosed embodiments are made for purposes of illustration and example only and not limitation. The scope of the present invention should be interpreted by terms of the appended claims.

INDUSTRIAL APPLICABILITY

As described above, the present invention suitably provides an image processing device, an image processing method, and an image processing program which enable distinction between a background surrounded by multiple cell nuclei and an inside-unstained nucleus in image processing for extracting cell(s) subjected to staining from an image obtained by photographing a tissue specimen.

REFERENCE SIGNS LIST

1 Inside-Unstained Nucleus
2 Background Surrounded By Multiple Cell Nuclei
31, 32, 33 Hole Region
1A Microscopic Image Acquiring Device
2A Image Processing Device
21 Controller
22 Operation Unit
23 Display
24 Communication I/F
25 Storage
26 Bus
3A Cable
100 Diagnosis Support Information Generation System

The invention claimed is:
1. An image processing device comprising:
a hardware processor that:
receives an image obtained by photographing a specimen subjected to staining;
extracts a region subjected to the staining from the image as a cell region;

extracts a hole region as a candidate region, the hole region being surrounded by the cell region and not being subjected to the staining;

extracts a feature amount of the candidate region;

determines, based on the feature amount, the candidate region is an unstained inner portion of a cell nucleus; and corrects the unstained inner portion of the cell nucleus.

2. The image processing device according to claim 1, wherein the hardware processor performs binarization processing so that the candidate region is a cell region.

3. The image processing device according to claim 1,
wherein the hardware processor sets a threshold value of the feature amount on a basis of at least one of a cancer type, progression of cancer, a method of collecting tissue, and a staining method, and determines, on a basis of the feature amount and the threshold value, whether or not the candidate region is a cell region.

4. The image processing device according to claim 1, wherein the feature amount includes a distinction result by a machine learning method.

5. The image processing device according to claim 1, wherein the feature amount includes at least one of an area, a circularity, a convex hull rate of an area, a number of concave/convex portions, and a curvature of the candidate region.

6. The image processing device according to claim 1, wherein the feature amount includes at least one of an average, a variation, and a difference of pixel value inside of or around the candidate region.

7. The image processing device according to claim 1, wherein the feature amount includes at least one of an edge intensity, an edge direction, and a variation in an edge direction of the candidate region.

8. An image processing method comprising:

inputting an image obtained by photographing a specimen subjected to staining;

extracting a region subjected to the staining from the image as a cell region;

extracting a hole region as a candidate region, the hole region being surrounded by the cell region and not being subjected to the staining;

extracting a feature amount of the candidate region;

determining, based on the feature amount, the candidate region is an unstained inner portion of the cell nucleus; and correcting the unstained inner portion of the cell nucleus.

9. A non-transitory computer readable medium storing an image processing program to cause a computer to:

receive an image obtained by photographing a specimen subjected to staining;

extract a region subjected to the staining from the image as a cell region;

extract a hole region as a candidate region, the hole region being surrounded by the cell region and not being subjected to the staining;

extract a feature amount of the candidate region;

determine, based on the feature amount, the candidate region is an unstained inner portion of a cell nucleus; and correct the unstained inner portion of the cell nucleus.

\* \* \* \* \*